United States Patent [19]

Beach et al.

[11] 4,382,153

[45] * May 3, 1983

[54] PROCESS FOR THE OLIGOMERIZATION OF ETHYLENE IN METHANOL

[75] Inventors: David L. Beach, Gibsonia; James J. Harrison, Glenshaw, both of Pa.

[73] Assignee: Gulf Research & Development Company, Pittsburgh, Pa.

[*] Notice: The portion of the term of this patent subsequent to Jan. 12, 1998, has been disclaimed.

[21] Appl. No.: 365,291

[22] Filed: Apr. 5, 1982

[51] Int. Cl.³ ............................................. C07C 2/02
[52] U.S. Cl. .................... 585/526; 585/511; 585/514; 585/515; 585/527; 585/531
[58] Field of Search .............. 585/511, 514, 515, 526, 585/527, 531

[56] References Cited

U.S. PATENT DOCUMENTS 4,310,716 1/1982 Beach et al. ..................... 585/527

*Primary Examiner*—Curtis R. Davis
*Attorney, Agent, or Firm*—Deane E. Keith; Forrest D. Stine; Joseph J. Carducci

[57] ABSTRACT

Ethylene is oligomerizied by reacting ethylene under an elevated pressure greater than about 700 pounds per square inch gauge (4826 kPa) in methanol in contact with a nickel ylide defined by the following Formula:

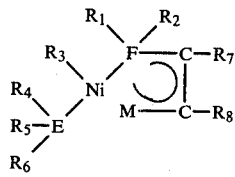

wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbon atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; and a hydrocarbyl group, such as defined above, carrying halogen, hydroxyl or alkoxy or aryloxy; provided that at least one, preferably from about one to about four, of each of $R_1$ to $R_8$ is a sulfonato group ($-SO_3^-$) or an alkyl, aryl, alkenyl, cycloalkyl, aralkyl or alkaryl group carrying a sulfonato group; M is sulfur or oxygen, preferably oxygen; E is phosphorus, arsenic, antimony or nitrogen, preferably phosphorus; and F is phosphorus, arsenic or antimony, preferably phosphorus. There is thus obtained a reaction product containing (A) a methanol phase having dissolved therein the nickel ylide catalyst and (B) an alpha-olefin phase. These two phases are then separated from each other to recover the alpha-olefin phase. The use of methanol as the solvent medium causes the reaction product to resolve itself into two phases: an upper phase containing most of the oligomer product, and a lower methanol phase carrying the catalyst dissolved therein. This permits easy separation of the product from the reaction mixture and also permits effective recycle of methanol with dissolved catalyst. The product obtained contains normal alpha-olefins having from about four to about 100 carbon atoms, generally from about four to about 50 carbon atoms.

38 Claims, No Drawings

PROCESS FOR THE OLIGOMERIZATION OF ETHYLENE IN METHANOL

BACKGROUND OF THE INVENTION

1. Field of the Invention

This invention relates to the use of nickel ylides to oligomerize ethylene in methanol as the solvent medium.

2. Description of the Prior Art

In our U.S. Pat. No. 4,310,716 dated Jan. 12, 1982, we have disclosed and claimed a process relating to the use of nickel ylides to oligomerize ethylene in methanol as the solvent medium, wherein the ethylene pressure in the reaction zone throughout the reaction period is maintained in the range of about 10 to about 700 psig (69.8 to 4827 kPa).

SUMMARY OF THE INVENTION

We have now found that ethylene can be oligomerized at relatively low operating temperatures and at pressures greater than about 700 psig (greater than about 4827 kPa) by reacting ethylene in methanol in contact with a nickel ylide defined by the following:

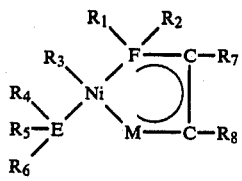

wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms, preferably from about one to about 10 carbon atoms; aryl radicals having from about six to about 20 carbon atoms, preferably from about six to about 10 carbon atoms; alkenyl radicals having from about two to about 30 carbon atoms, preferably from about two to about 20 carbon atoms; cycloalkyl radicals having from about three to about 40 carbon atoms, preferably from about three to about 30 carbon atoms; aralkyl and alkaryl radicals having from about six to about 40 carbon atoms, preferably from about six to about 30 carbon atoms; a halogen radical selected from the group consisting of fluorine, chlorine, bromine and iodine, preferably chlorine; a hydroxyl group; an alkoxy or aryloxy group; and a hydrocarbyl group, such as defined above, carrying halogen, hydroxyl or alkoxy or aryloxy; provided that at least one, preferably from about one to about four, of each of $R_1$ to $R_8$ is a sulfonato group ($-SO_3-$) or an alkyl, aryl, alkenyl, cycloalkyl, aralkyl or alkaryl group carrying a sulfonato group; M is sulfur or oxygen, preferably oxygen; E is phosphorus, arsenic, antimony or nitrogen, preferably phosphorus; and F is phosphorus, arsenic or antimony, preferably phosphorus. There is thus obtained a reaction product containing (A) a methonol phase having dissolved therein the nickel ylide catalyst and (B) an alpha-olefin phase. These two phases are then separated from each other to recover the alpha-olefin phase. Specific examples of nickel ylides that can be used herein, and methods for preparing the same, are defined in our said U.S. Pat. No. 4,310,716, which nickel ylides and processes are incorporated herein by reference.

As in our U.S. Pat. No. 4,310,716, the use of methanol as the solvent medium causes the reaction product to resolve itself into two phases: an upper phase containing most of the oligomer product and a lower methanol phase carrying the catalyst dissolved therein. This permits easy separation of the product from the reaction mixture and also permits effective recycle of methanol with dissolved catalyst. The product obtained contains normal alpha-olefins having from about four to about 100 carbon atoms, generally from about four to about 50 carbon atoms.

The only components required in the reaction zone are ethylene, the nickel ylide catalyst and methanol as carrier or solvent. If desired, methanol need not be used alone as solvent but can be used with up to about 50 weight percent, preferably from about five to about 30 weight percent, of the oligomer product dissolved therein. The order of addition of these components (ethylene, catalyst and methanol) to the reaction zone is not critical, although it is preferred that catalyst and methanol first be heated to reaction temperature and then to add rapidly ethylene to the desired pressure. The reaction can be carried out in any manner that assures contact between ethylene and catalyst, for example, in a batch reactor or in a continuous stirred tank reactor.

The amount of nickel ylide catalyst used, which is soluble in the methanol solvent, will be such that its concentration therein will be in the range of about 0.0001 to about 1.0 moles per liter of solvent, preferably in the range of about 0.0005 to about 0.1 mole per liter of solvent. Ethylene is added to the reaction zone as needed, but throughout the reaction period the ethylene pressure in the reaction zone is maintained at a level greater than about 700 psig (4826 kPa), preferably greater than about 700 psig (4826 kPa), but below about 3000 psig (20,955 kPa); most preferably greater than about 700 psig (4827 kPa), but below about 200 psig (13,970 kPa). The reaction temperature can be in the range of about $-20°$ to about 200° C., preferably in the range of about 20° to about 100° C. The contact time (the length of time between the exposure of catalyst to ethylene and the separation of unreacted ethylene and/or reaction product from the catalyst) can be in the range of about one minute to about 72 hours, preferably in the range of about 10 minutes to about 24 hours. Throughout the reaction period the reaction mixture is agitated. Ethylene conversion under optimum reaction conditions can be in excess of about 90 percent and can reach up to about 99 percent.

At the end of the reaction period, the gaseous components that may be present in the reaction product, for example, unreacted ethylene, $C_4$ olefins, etc., are flashed therefrom and ethylene and, if desired, other gaseous components and even liquid components that may have been entrained with the off-gases, can be recycled to the reaction zone. The remainder of the reaction product will consist of two liquid phases: an upper phase containing the bulk of the desired ethylene oligomerization product and, possibly, traces of methanol; while the lower phase will contain methanol, catalyst and, possibly, up to about 50 weight percent, based on the total lower phase, of ethylene oligomer product, but generally from about five to about 30 weight percent of ethylene oligomer product. These two phases can be separated from each other by any conventional means, for example, by decantation, by centrifuging, etc. In a preferred embodiment, the lower methanol phase is recycled to the reaction zone for use therein. The components of the upper liquid phase can be separated into any suitable fraction by any suitable means, for example, by fractional distillation.

DESCRIPTION OF PREFERRED EMBODIMENTS

The process defined and claimed herein can be illustrated by the reference to the following runs.

Into a one-liter autoclave there was charged 0.2 grams (0.25 millimole) of a specific nickel ylide dissolved in 100 milliliters of methanol. The nickel ylide (identified as Compound 9 in Example III of our U.S. Pat. No. 4,310,716) can be identified as follows:

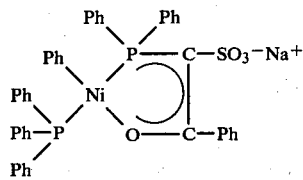

In the above, Ph refers to the phenyl radical. During the reaction, precautions were taken to exclude air contamination by performing the reactions in an argon atmosphere. The reaction mixture was then heated to 80° C. in Runs Nos. 1 and 2 and to 50° C. in Runs Nos. 3 and 4, and pressured with ethylene to obtain a selected ethylene pressure therein:

1000 psig (6895 kPa) in Run No. 1
800 psig (5516 kPa) in Runs Nos. 2 and 3
500 psig (3448 kPa) in Run No. 4.

The reaction mixture was stirred during the reaction period of three hours in Runs Nos. 1, 2 and 3, and two hours in Run No. 4, during which reaction periods the pressures and temperatures were maintained at the indicated levels. At the end of the defined reaction periods, the reaction mixtures were cooled to room temperatures and thereafter vented carefully over a period of four hours to remove ethylene and any other gaseous products that might have been removed concurrently therewith. The liquid reaction product resolved itself into two separate and distinct phases: an upper liquid phase containing the desired ethylene oligomer, and a lower methanol phase containing dissolved nickel ylide catalyst. The two phases were separated by decantation. The data obtained are tabulated below in Table I.

TABLE I

| Run No. | Temp. °C. | Reaction Pressure, psig (kPa) | Activity (moles of ethylene reacted per mole of catalyst during reaction period) |
|---|---|---|---|
| 1 | 80 | 1000 (6895) | 428 |
| 2 | 80 | 800 (5516) | 3900 |
| 3 | 50 | 800 (5516) | 3000 |
| 4 | 50 | 500 (3448) | 4800 |

The above data clearly show that nickel ylides can be used to oligomerize ethylene in methanol as a solvent medium at ethylene pressures greater than about 700 psig (4827 kPa). In our U.S. Pat. No. 4,310,716 we had concluded, on the basis of Runs Nos. 7 and 8 of Table IV, that little or no oligomerization would occur in said reaction using ethylene pressures in excess of about 700 psig (4827 kPa). In the runs in the patent we removed the unreacted ethylene from the reaction product rather quickly, over a period of about two hours, while herein such removal was carried out more carefully and over a period of four hours. We believe that in the runs of the patent, ethylene oligomerization product was inadvertently removed from the reaction product along with the unreacted ethylene and therefore was unaccounted for. Herein, while some ethylene oligomerization product may have also been inadvertently removed from the reaction system, enough was found in the reaction product to show that nickel ylides can be used to oligomerize ethylene in methanol as a solvent medium at ethylene pressures greater than about 700 psig (4827 kPa).

Obviously, many modifications and variations of the invention, as hereinabove set forth, can be made without departing from the spirit and scope thereof, and therefore only such limitations should be imposed as are indicated in the appended claims.

We claim:

1. A process for oligomerizing ethylene to normal alpha-olefins and recovering said olefins from the reaction product which comprises reacting ethylene under an elevated pressure greater than about 700 pounds per square inch gauge in methanol in contact with a nickel ylide defined by the following formula:

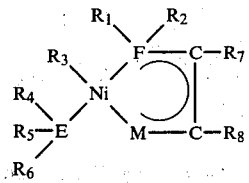

wherein $R_1$, $R_2$, $R_3$, $R_4$, $R_5$, $R_6$, $R_7$ and $R_8$ are either alike or different members selected from the group consisting of hydrogen, alkyl radicals having from about one to about 24 carbon atoms; aryl radicals having from about six to about 20 carbon atoms; alkenyl radicals having from about two to about 30 carbon atoms; cycloalkyl radicals having from about three to about 40 carbon atoms; aralkyl and alkaryl radicals having from about six to about 40 carbon atoms; halogen radicals, hydroxyl, alkoxy and aryloxy groups, and hydrocarbyl groups carrying halogen, hydroxyl alkoxy and aryloxy groups, provided that at least one of each of $R_1$ to $R_8$ radicals is a sulfonato group or an alkyl, aryl, alkenyl, cycloalkyl, aralkyl or alkaryl group carrying a sulfonato group; M is sulfur or oxygen; E is phosphorus, arsenic, antimony or nitrogen; and F is phosphorus, arsenic or antimony, to obtain a reaction product containing (A) a methanol phase having dissolved therein said nickel ylide and (B) an alpha-olefin phase, and then separating said phases from each other to recover said alpha-olefin phase.

2. A process as defined in claim 1 wherein the sulfonato group is in $R_4$, $R_5$ and/or $R_6$ and at least one of $R_4$, $R_5$ and $R_6$ is aryl.

3. A process as defined in claim 1 wherein the sulfonato group is in $R_1$, $R_2$ and/or $R_3$.

4. A process as defined in claim 1 wherein $R_7$ comprises a sulfonato group.

5. A process as defined in claim 1 wherein E and F are both phosphorus and M is oxygen.

6. A process as defined in claim 2 wherein E and F are both phosphorus and M is oxygen.

7. A process as defined in claim 3 wherein E and F are both phosphorus and M is oxygen.

8. A process as defined in claim 4 wherein E and F are both phosphorus and M is oxygen.

9. A process as defined in claim 6 wherein each of $R_4$, $R_5$ and $R_6$ is phenyl, one of which is substituted with a sulfonato group.

10. A process as defined in claim 9 wherein each of $R_1$, $R_2$, $R_3$ and $R_8$ is phenyl and $R_7$ is hydrogen.

11. A process as defined in claim 7 wherein each of $R_1$, $R_2$ and $R_3$ is phenyl, one of which is substituted with a sulfonato group.

12. A process as defined in claim 11 wherein each of $R_4$, $R_5$, $R_6$ and $R_8$ is phenyl and $R_7$ is hydrogen.

13. A process as defined in claim 8 wherein each of $R_1$, $R_2$, $R_3$, $R_4$, $R_5$, $R_6$ and $R_8$ is phenyl and $R_7$ is a sulfonato group.

14. A process as defined in claim 13 wherein said ylide is in the form of its sodium salt.

15. A process as defined in claim 1 wherein said methanol phase contains up to 50 weight percent of the oligomer product dissolved therein.

16. A process as defined in claim 1 wherein said methanol phase contains from about five to about 30 weight percent of the oligomer product dissolved therein.

17. A process as defined in claim 13 wherein said methanol phase contains up to 50 weight percent of the oligomer product dissolved therein.

18. A process as defined in claim 13 wherein said methanol phase contains from about five to about 30 weight percent of the oligomer product dissolved therein.

19. A process as defined in claim 14 wherein said methanol phase contains up to 50 weight percent of the oligomer product dissolved therein.

20. A process as defined in claim 14 wherein said methanol phase contains from about five to about 30 weight percent of the oligomer product dissolved therein.

21. A process as defined in claim 1 wherein said ethylene and said nickel ylide are contacted at a temperature of from about −20° to about 200° C. for about one minute to about 72 hours.

22. A process as defined in claim 1 wherein said ethylene and said nickel ylide are contacted at a temperature of from about 20° to about 100° C. for about 10 minutes to about 24 hours.

23. A process as defined in claim 13 wherein said ethylene and said nickel ylide are contacted at a temperature of from about −20° to about 200° C. for about one minute to about 72 hours.

24. A process as defined in claim 13 wherein said ethylene and said nickel ylide are contacted at a temperature of from about 20° to about 100° C. for about 10 minutes to about 24 hours.

25. A process as defined in claim 14 wherein said ethylene and said nickel ylide are contacted at a temperature of from about −20° to about 200° C. for about one minute to about 72 hours.

26. A process as defined in claim 14 wherein said ethylene and said nickel ylide are contacted at a temperature of from about 20° to about 100° C. for about 10 minutes to about 24 hours.

27. A process as defined in claim 1 wherein said metal ylide is present in the range of about 0.0001 to about 1.0 moles per liter of solvent.

28. A process as defined in claim 1 wherein said metal ylide is present in the range of about 0.0005 to about 0.1 moles per liter of solvent.

29. A process as defined in claim 13 wherein said metal ylide is present in the range of about 0.0001 to about 1.0 moles per liter of solvent.

30. A process as defined in claim 13 wherein said metal ylide is present in the range of about 0.0005 to about 0.1 moles per liter of solvent.

31. A process as defined in claim 14 wherein said metal ylide is present in the range of about 0.0001 to about 1.0 moles per liter of solvent.

32. A process as defined in claim 14 wherein said metal ylide is present in the range of about 0.0005 to about 0.1 moles per liter of solvent.

33. A process as defined in claim 1 wherein the ethylene pressure is maintained at a level greater than about 700 pounds per square inch gauge but below about 3000 pounds per square inch gauge.

34. A process as defined in claim 1 wherein the ethylene pressure is maintained at a level greater than about 700 pounds per square inch gauge but below about 2000 pounds per square inch gauge.

35. A process as defined in claim 1 wherein the methanol phase is recycled to the reaction zone for use therein.

36. A process as defined in claim 13 wherein the methanol phase is recycled to the reaction zone for use therein.

37. A process as defined in claim 14 wherein the methanol phase is recycled to the reaction zone for use therein.

38. A process as defined in claim 1 wherein unreacted ethylene is recycled to the reaction zone for use therein.

* * * * *